(12) United States Patent
Singer et al.

(10) Patent No.: US 8,395,376 B2
(45) Date of Patent: Mar. 12, 2013

(54) METHOD AND APPARATUS FOR MAGNETIC RESPONSE IMAGING

(75) Inventors: Jerome R. Singer, Berkeley, CA (US); Glen Stevick, Berkeley, CA (US); David Rondinone, Berkeley, CA (US); John Zalabak, Berkeley, CA (US)

(73) Assignee: 4D Imaging, Inc., Berkeley, CA (US)

( * ) Notice: Subject to any disclaimer, the term of this patent is extended or adjusted under 35 U.S.C. 154(b) by 236 days.

(21) Appl. No.: 12/927,756

(22) Filed: Nov. 22, 2010

(65) Prior Publication Data

US 2012/0126798 A1     May 24, 2012

(51) Int. Cl.
*G01R 33/12*     (2006.01)
(52) U.S. Cl. .................. 324/229; 324/219; 324/200
(58) Field of Classification Search .................. None
See application file for complete search history.

(56) References Cited

U.S. PATENT DOCUMENTS 8,174,259 B2 * 5/2012 Hattersley et al. ............ 324/248
8,284,560 B2 * 10/2012 Iravani et al. ................. 361/760

* cited by examiner

*Primary Examiner* — Jermele M Hollington
*Assistant Examiner* — Trung Nguyen
(74) *Attorney, Agent, or Firm* — Howard Cohen

(57) ABSTRACT

An apparatus and method for identifying, measuring, and monitoring metal loss through corrosion or other deleterious factors in ferromagnetic piping and ferromagnetic objects. Drive coils secured to the object are driven to emit a magnetic field which is transmitted through the object by magnetic domains in the object. Response coils detect the magnetic domains and generate a response signal. The drive and response signals can penetrate insulating materials and non-ferromagnetic metallic coverings of the piping and vessels. The system operates reiteratively over an extended period of time, e.g., months or years, to detect loss of magnetic domains which is an important indicator of corrosion and deterioration of the object.

21 Claims, 4 Drawing Sheets

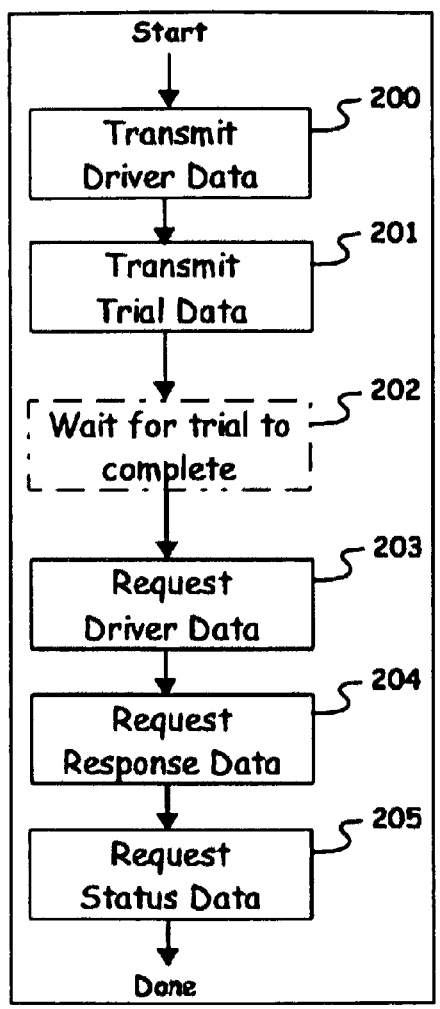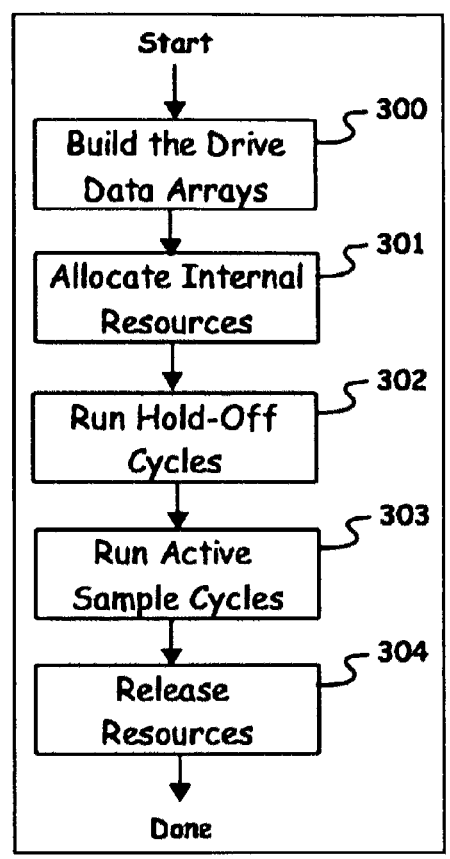
FIG. 3
FIG. 4

METHOD AND APPARATUS FOR MAGNETIC RESPONSE IMAGING

CROSS-REFERENCE TO RELATED APPLICATIONS

Not applicable.

FEDERALLY SPONSORED RESEARCH

Not applicable.

SEQUENCE LISTING, ETC ON CD

Not applicable.

BACKGROUND OF THE INVENTION

1. Field of the Invention

The present invention relates to apparatus and methods which can be utilized for identifying, measuring, and monitoring metal loss through corrosion or other deleterious factors in metallic materials and especially in ferromagnetic piping and ferromagnetic vessels.

2. Description of Related Art

The following patents and publications exemplify the state of the art in systems for detecting corrosion in metallic systems, particularly pipes and pipelines.

Patent Publication No. US2002/0153249 by Eric Atherton describes a metallic corrosion monitoring system which employs the measurement of electrical current flow in the metal. This method is not as sensitive as the present invention and its measurement of magnetic flux for the detection of corrosion. There are a number of similar patents which depend upon the electrical conductivity of the metal to detect corrosion. In practice, it is difficult to detect the small changes in conductivity of a metal as it corrodes, since the effects of the corrosion will generally be very small compared to the remaining metal. The present invention does not utilize the conductivity of the metal in its application.

U.S. Pat. No. 4,400,782 by Masashi Ishikawa describes a system of using a pipe as a transmission line using the conductivity of the pipe. It is not practicable for continuous monitoring of a pipeline for corrosion because the system stability of the transmission line is not sensitive to small levels of corrosion. The present invention does not utilize the conductivity of the pipe in monitoring the pipe.

U.S. Pat. No. 4,107,605 by Robert Hudgell describes a method of testing metallic pipelines using eddy current sensing coils It is not suitable for long term monitoring of pipelines for corrosion as per the present patent application, and the present invention does not use eddy currents.

Patent Publication No. US2009/0058406A1 by Mochimitsu Komori describes a method of measuring the corrosion state of a magnetic material. It utilizes a two stage method of magnetization and is distinct from the present invention which uses a continuous AC magnetization procedure.

Patent No. 0126422 by Alfred Crouch, et. al., describes a method of measuring a surface defect in an electrically conducting material using a pair of resonant coils. It is basically an eddy current array which is substantially different from the present invention which does not use eddy current technology.

U.S. Pat. No. 7,521,917 by Katragadda et. al., describes a method of detecting material integrity which drives a current through the material and then utilizes a sensing system for the magnetic field induced in the material. It is designed for testing train rails. The present invention does not drive a current through the pipe or vessel under consideration, and is substantially different in configuration and in application.

U.S. Pat. No. 7,362,097 by Brown, et. al., describes a pipeline inspection system where the apparatus design is for the movement of flexible coils that are pushed through the interior of the pipeline. The present invention uses fixed coils on the exterior of the pipeline and does not use any movement of these coils.

Patent Publication No. US2010/0017137A1 by Legandre Emmanual describes a method of measuring the physical parameters of a pipe by comparing the magnetic permeability to the electrical conductivity using coils within a pipe. The method is substantially different from the present invention in method and in coil configurations.

U.S. Pat. No. 7,6229,116 by Gerald Meeten, et. al., describes a three coil system for measuring structural features of a bore hole casing. The system moves through the interior of the bore hole and is very different from the present invention which has no moving parts.

U.S. Pat. No. 4,611,170 by Roderick Stanley, et. al. describes a method of inspecting ferromagnetic pipes which features three movable axially split spools of wire and saturation levels of magnetic flux in the pipe. It is moved along the pipe and utilizes differential voltages of the two end pickup coils. The system is not a monitoring system for the pipe as per the present patent description.

There are many patents for measuring metallic integrity using eddy current systems. The present invention is not an eddy current system, and does not use eddy current technology. Also, the present invention utilizes computer(s), and digital processor(s) in order to provide a stable method of monitoring and correcting for the variable factors which affect the detection of corrosion and deterioration of pipelines and vessels.

BRIEF SUMMARY OF THE INVENTION

The present invention relates to apparatus and methods which can be utilized for identifying, measuring, and monitoring metal loss through corrosion or other deleterious factors in metallic materials and especially in ferromagnetic piping and ferromagnetic vessels. The excitation and response signals can penetrate insulating materials and non-ferromagnetic metallic coverings of the piping and vessels. That provides an important advantage for use in existing pipelines which usually have such coverings in place. Computer monitoring of pipelines for metal loss over an extended period of time, e.g., months or years, is important for the determination of the safety and integrity of the pipe. The system is designed to provide very stable measurements in order to detect small levels of corrosion and deterioration.

BRIEF DESCRIPTION OF THE DRAWING

FIGS. 3 and 4 are flow charts illustrating the method of the present invention from the host system perspective and the node perspective, respectively.

DETAILED DESCRIPTION OF THE INVENTION

The present invention generally comprises apparatus and methods which can be utilized for identifying, measuring, and monitoring metal loss through corrosion or other deleterious factors in metallic materials and especially in ferromagnetic piping and ferromagnetic vessels.

Figure 1A:
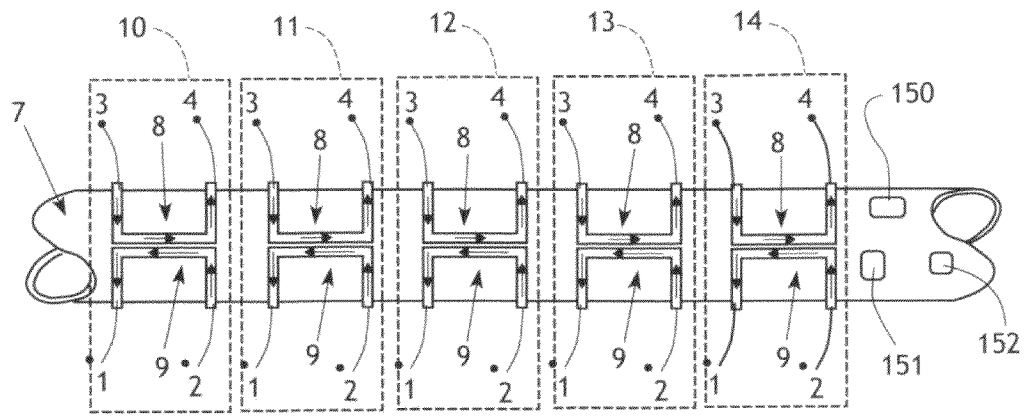
FIG. 1A is a plan view of one embodiment of the drive coils and response coils of the magnetic response imaging system of the present invention.
Figure 1B:
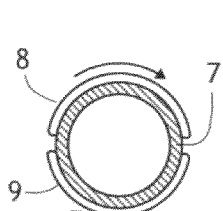
FIG. 1B is a cross-sectional elevation of the invention, taken along line 1B-1B of FIG. 1.
Figure 1C:
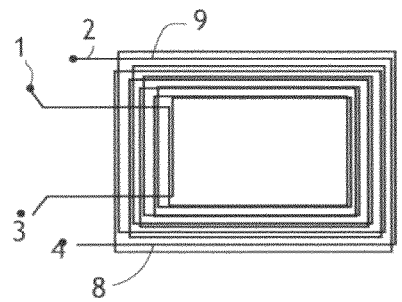
FIGS. 1C and 1D are plan views of a rectangular and ovoid coil layout as used in the present invention.
Figure 1D:
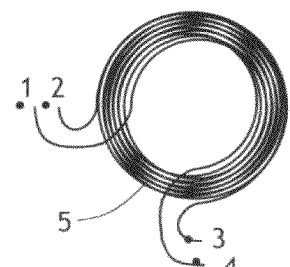
Figure 5:
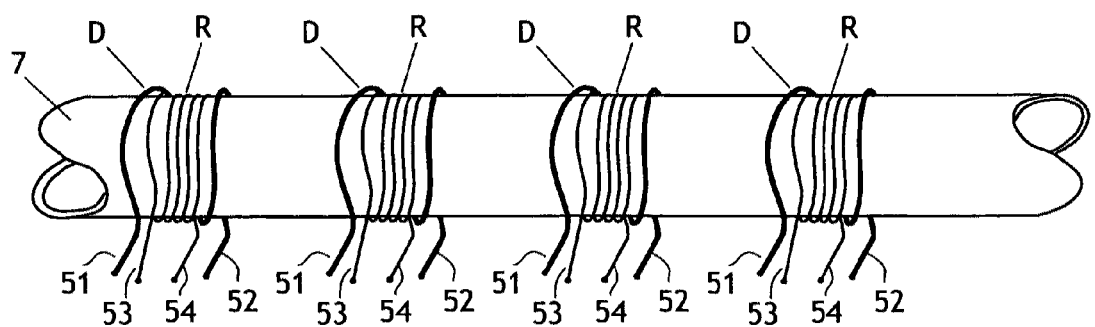
FIG. 5 is a plan view of a further embodiment of the drive coils and response coils of the magnetic response imaging system of the present invention.

FIG. 5 depicts a set of coils, each with a driver coil and a receiver coil either wound together or close by, as shown in FIG. 1D, mounted circumferentially about a section of a pipeline 7. The heavier coils D (shown in darker line), have ends 51 and 52 that are connected to be driven by a signal source to generate an electromagnetic field. The coils are multiplexed so that they may be driven individually or in groups, as described below. The lighter coils R (shown in fine line) have ends 53 and 54 and are the receiving coils which generate a response signal stimulated by the electromagnetic signal transferred by the magnetic domains of the pipeline sidewall.

Figure 1E:
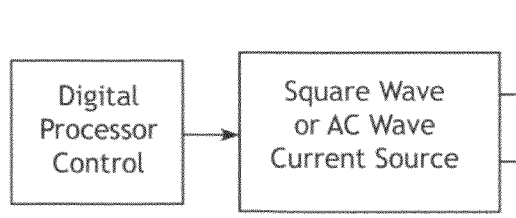
FIGS. 1E and 1F are functional block diagrams of portions of the electronic circuitry of the present invention.

The AC or fluctuating current from the signal source shown in FIG. 1E drive the coils in a multiplexed sequential mode that causes the pipe segments under each coil in turn to cause the magnetic domains of the pipe to align in a forward and backward direction. The domain motion induces voltages in the neighboring receiving coils, the voltage appearing across leads 53 and 54 as the response signal. The levels of the induced voltages are dependent upon the number of domains within the pipe sidewall. Deterioration of the ferromagnetic pipe in the regions and neighboring regions of the drive coils will reduce the induced voltages in the receiving coils R. Using this relationship enables the system of the invention to monitor the pipe 7 over long periods of time for corrosion or other deteriorations of the pipe integrity. To accomplish this effectively, a digital processor or a computer system is required.

In order to monitor the pipe for such deterioration, it is necessary to provide a very stable driver source for the coils D that generate the magnetic fields, and to provide analysis and correction for the driver source variability over long periods of time. In addition, it is necessary to monitor and correlate temperature variations and correct for these over long periods of time. These correlations can be accomplished by digital control of the drive signal, and monitoring and correcting for the variations of the drive signal and by digitally measuring the temperature of the pipe and environs and correcting for these variations as well as any other random or periodic interfering signals over the course of time. The apparatus and method for this systematic corrective stability is described below.

The coils shown in FIG. 5 are not easily applied to installed pipelines. Therefore, another type of coil arrangement, shown in FIG. 1A, may be used for simpler installation on existing pipelines (or pipelines under construction, if desired). The coil arrangement comprises a plurality of saddle units 10, 11, 12, 13, 14, etc., Each saddle unit is comprised of a pair of coils 8 and 9 that are wound together and have terminal ends 3, 4 and 1, 2, respectively, as shown in FIG. 1C. The saddle coils are connected in a mode which allows the currents to flow circumferentially around the pipe for both the driver coils and the receiver coils, as suggested by the arrows on the coil representations 8 and 9 in FIGS. 1A and 1B. The saddle coils perform the same function as the coils shown in Figure A, and provide a simpler method of application to the pipeline 7.

FIGS. 1A-1F illustrate one configuration of the magnetic response imaging (MRI) system of the invention. FIGS. 1A and 1B illustrate a portion of a pipeline 7 and show one example of the MRI system. A fundamental principle of this invention is the transformation of electrical energy into magnetic energy in the form of moving magnetic domains, and the further transformation of moving magnetic domains into electrical energy which is easily measured. Deterioration of the pipe sidewall causes a loss of magnetic domains. That loss will be manifest as a loss of energy transfer via magnetic domains moving through the pipe, and is accurately measurable. The coils 8 and 9, which are designed to conform to the outer surface of the pipeline 7 are arranged so as to provide excitation magnetic fields and detection of the delayed response detection signal as will be described below. Another very useful coil configuration is the saddle coils shown in FIG. 1 as completely encasing the pipe in contrast to the drawing which shows them in pairs to assist each other in enclosing the pipe. The purpose of these coils is the same in each configuration, namely to provide a magnetic field to excite the magnetic domains and a secondary set of coils to detect variations in the amount of magnetic domains due to pipe deterioration.

FIG. 1C shows one embodiment of a configuration of the wire coils which are employed to monitor the pipelines. Coils 8 and 9 may be wound about a rectangular mandrel and formed in a nominal plane. The coils is then bent out of the planar configuration into a curved shape that describes a portion of a cylinder and conforms to the curvature of the outer surface of pipe 7. The coils may also be applied to existing insulation of the pipeline, the insulation typically being non-ferromagnetic material that does not interfere with the magnetic signal. The rectangular shape of coils 8 and 9 as shown is one example, but other shapes such as the circular coils 5 of FIG. 1D or the like which curved out of the usual planar configuration to circumscribe the pipe or conform to the shape of the pipe as in FIG. 1B will also work equally well. The reason for illustrating rectangular coils or almost rectangular coils is that they are efficiently and easily installed on pipelines. FIG. 1B shows rectangular shaped coils secured on the pipe 7, shown in cross sectional elevation. FIG. 1A shows a plurality of paired coils arranged in a manner such that each pair of coils 8, 9, reinforce each other in providing a current directed so as to circumscribe the pipe 7 when activated with a current source connected to each and all of the wires 1 and 2. Each pair of the set of coils, 8, 9, is oriented to reinforce each other in providing current flow in the same direction circumscribing the pipe, thus applying the same magnetic field to the pipe 7 under inspection. As described in the multiplexing system of FIG. 2, neighboring coil sets are selected to receive the driving currents in wires 1 and 2, and the response signals manifest in wires 3 and 4. Once two or three sets have been driven and their response measured, as for example sets 10, 11, or 10, 11, and 12, then the driver and the response measurement moves on in the multiplexing system to another coil set, such as 11, and 12, or 11, 12, and 13. Following that set of excitation and measurement, the multiplexing system moves on to coil sets 12, and 13, or 12, 13, and 14. The multiplexing system goes on from there to select the next two or three coils and their response and continues on for all of the coil sets on the pipeline.

Figure 1F:
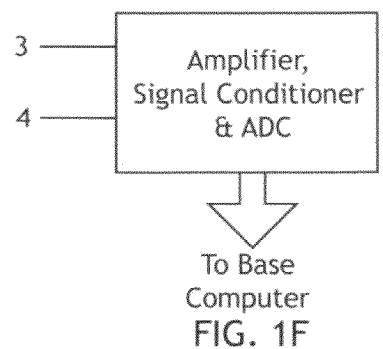
Figure 2:
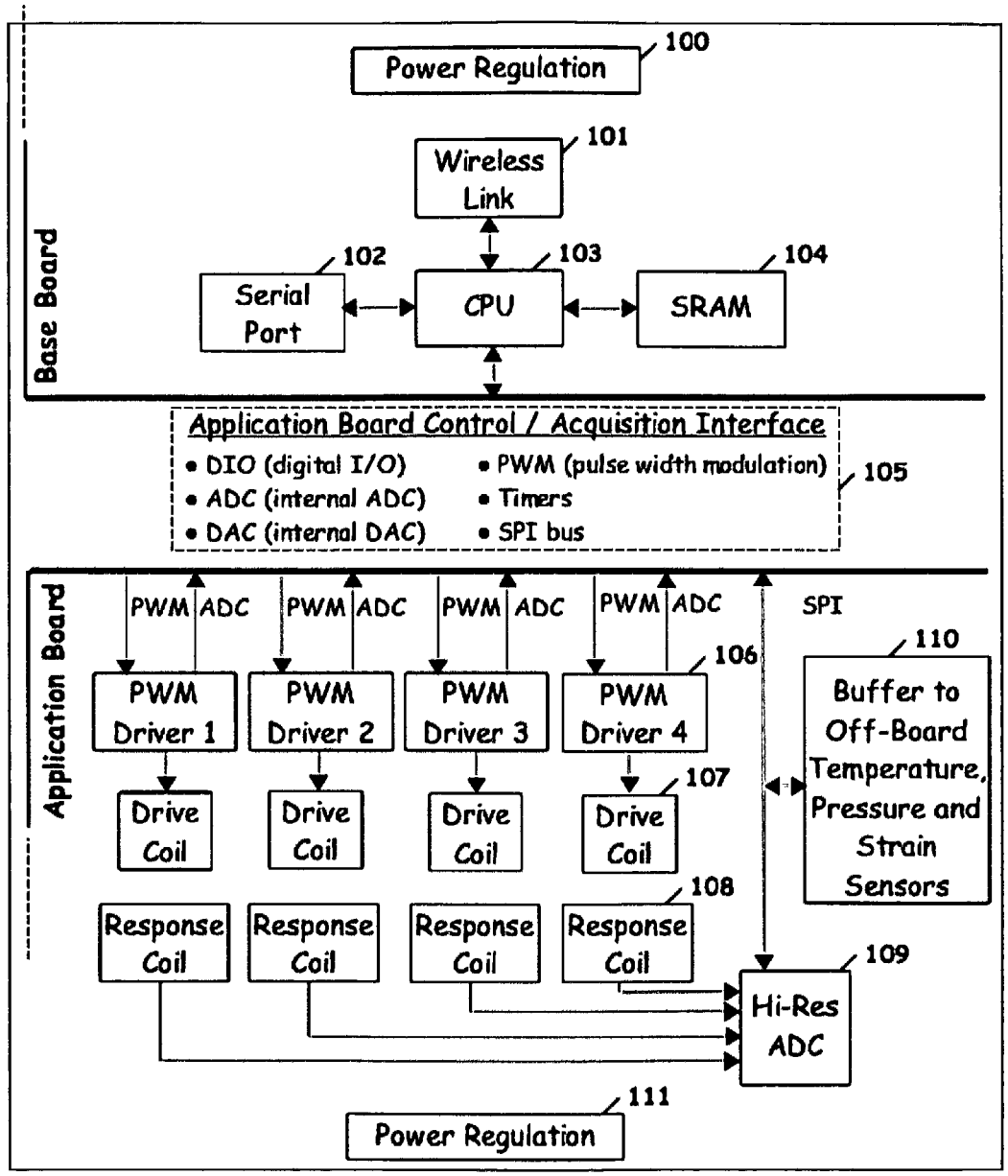
FIG. 2 is a functional block diagram of the base board and application board electronic systems of the present invention.

FIG. 1E shows a time varying power source which is either pulsed DC or AC and is stabilized and controlled by a central processor or computer system as in FIG. 2, The power source is connectable in turn to all of the drive coils 8 with leads labeled 1 and 2. The carefully regulated and computer controlled current source from ID drives the coils 8 to produce a controlled magnetic field that causes the periodic alignment of magnetic domains in the pipeline in the forward or backward direction along or about the pipeline axis direction. The moving magnetic domains in turn induce a voltage in the respective detector coils 9. The digitization of the driver signals at terminals 1 and 2 allows flexibility in determining the voltage level observed in the terminals 3 and 4 of coil(s) 9. As shown in FIG. 1F, the signals from each detector coil 9 are connected to an amplifier, signal conditioner, and analog to digital converter, (A/D), in FIG. 1E, and conducted to the base computer, which is more fully described in FIG. 2. The digital signal output of the A/D is proportional to the number and size of magnetic domains and their driven frequency. The driven frequency from a source shown in FIG. 1E, and in more detail in FIG. 2, is generally fixed at a relatively low ac frequency, usually less than 200 Hz.

Eddy currents may cause some energy loss, but we are not measuring or are we interested in those losses, but are only concerned with the net number of magnetic domains that are activated by the drive coils 8 in the forward direction. Eddy currents are in the opposite direction from the driven direction of the magnetic domains and are not a concern nor are they measured.

The detection of the amplitudes of the signal at the detection coils is proportional to the number of domains and to the frequency of the square wave or AC wave generated by the digitally controlled generator in FIG. 1E, which is controlled by a central processor or computer so as to be constant and consistent. Therefore the amplitude of the detected signal is accurately proportional to the number of magnetic domains that are within the pipe wall and are between the driven coils and the respective neighboring detector coils. Since the number of domains is dependent on the ferromagnetic pipe, and pipe corrosion products are practically always non-ferromagnetic, the detection signals are an accurate measure of the integrity of the pipe, or alternatively, the degree or degradation of the pipe.

The amplifier, analog to digital converter, (ADC), and transmission system in FIG. 1F, and shown in more detail in FIG. 2, provides signal conditioning of the detector coils, and sends the digital signal either to a central base computer or a local microprocessor for further analysis of the received signal. It is helpful that the electronics in the driver and receiver system be stable for long periods in order to detect and measure minor corrosions of the pipe.

Temperature variations, and to a lesser degree, strains and pressure variations affect magnetic permeability which relates to changes in the number of active magnetic domains and should be compensated for in order to obtain long term stability of the measurements. Therefore the electronic detection system incorporates a temperature sensors 150, such as thermisters, transistors, or thermocouples to correct for temperature variations and provide stable long term measurements. In addition, strain sensors 151 provide information about significant strains in the pipeline which may affect its lifetime, and pressure sensors 152 provide additional information which may affect the integrity of the pipeline. All of these sensors, as well as the detector coil signals are connected via wires or wirelessly to central processor(s) or computer(s), as shown in FIG. 2, which provide the status of the pipe by calculating all of the sensed parameters and monitoring the health of the pipeline.

Since the digital signal appearing at terminals 3 and 4 is dependent upon the number of magnetic domains of the ferromagnetic pipe, any variation in the pipe integrity will show up as a change in the voltage induced in the detector coil. Therefore this configuration will enable the detection of corrosion or deterioration of the pipe whether inside or outside of the pipe.

In more detail, the A/D converter in FIG. 1F provides for a sensitive detection in variations of the number of magnetic domains and therefore the amount of ferromagnetic pipe material which transmits the magnetic field from one set of coils to the next set of coils. The changing magnetic field due to the A.C. source in FIG. 1E which drives the set of coils through connections 1 and 2 causes the magnetic domains to align along the pipe and then reverse their alignment in phase with the driver AC frequency in FIG. 1E. This changing magnetism then induces a voltage in the local and neighboring coils which is proportional to the initial magnetic fields induced and to the integrity of the pipe. As the ferromagnetic pipe partially deteriorates to iron oxide, iron sulfide or other common non-magnetic corrosion products, the number of magnetic domains is lessened, and fewer domains are left to transmit magnetic domains to the neighboring coils. By periodically monitoring the voltage induced in neighboring and co-axial coils, the degree of corrosion or other deterioration of the pipe is readily measured over time.

In FIG. 1A each set of coils are identical and symmetrical. This symmetry is not necessary but is convenient when the pipeline is uniform. The system works just as well when the pipeline bends or has other variations because the monitoring system is based upon the changes over time to the number of magnetic domains in any segment of the pipeline. The initial measurements of the pipeline determine the base levels of the number of magnetic domains in the pipeline and subsequent measurements determine the changes in the number of magnetic domains. Thus the system is effectively self-calibrating.

All of the measurements are multiplexed. That is, any set of coils can be addressed and interrogated to determine the integrity of the pipe in the neighborhood of the addressed coils. It is straightforward to use separate receiving and transmission coils, as described above. However, in an alternative embodiment of the invention every coil may comprise both a receiving coil and a transmission coil. This configuration is a further example of the invention and functions just as well as the previous embodiment.

In some cases, it is not practicable to use symmetrical arrangements of coils, as for example with bends in the pipeline. In all cases, the system will work well because the voltages of the asymmetrical coils, as well as with the symmetrical coils, when transferred to the computer system, will be monitored for corrosion by automatically providing a base level from which corrosion or deterioration will show losses in the detector coils. The base level and subsequent measurements may encompass other parameters which can be determined by computer calculation and may consider temperature, strain, pressure, and any other factors that provide a significant change in the measurement of the pipeline condition.

A principal feature of the invention is that the driving coils are driven by time varying currents which cause the magnetic domains to oscillate, and neighboring or co-axial coils which have a voltage induced into them by the numerical level of time-varying magnetic domains. Since the level of magnetic domains is proportional to the amount of pipe under and between the coils, the voltage induced into the receiving coils which is observed at terminals 3 and 4 is proportional to the integrity of the pipe. As the pipe corrodes, the voltage at terminals 3 and 4 will lessen since fewer domains will be activated by the AC driven coils at terminals 1 and 2.

It is very useful to multiplex the coil drivers and receivers in sets so that the power source to provide AC power to sets of coils at terminals 1 and 2 and the receiver coils with terminals 3 and 4 does not use very much electrical power. One method of multiplexing the coil drivers and receivers involves using a network of driver/receiver coil control nodes. Each node in such a system is responsible for the activation of its attached driving coil(s) and for the monitoring its attached sense coil(s). Such a system allows the application of the drive signal and the receipt of the response signal to a small section of the total system, thus providing economy of power. The advantage of such a multiplexing method is not limited to power savings. This method of multiplexing also allows for scaling the system. Thus, the same fundamental system may be applied to a short section of pipe or to an intercontinental pipeline. This network of nodes can be controlled by sending packets of information across any one of a number of existing network technologies. Such technologies can include both wired and wireless systems, given that the system has sufficient bandwidth.

Under certain circumstances it is sometimes useful to drive coils controlled by other than the sensing node while ensuring that that the same current flows through all coils. This is particularly important when it is necessary to maintain the balance of differential coil measurements. This may be done by interconnecting the nodes so that the coil connections immediately adjacent to a given node may be connected to its opposite neighbor node. In this manner, the driving signal may be applied to one terminal of a given coil, while its opposite terminal is connected to a coil several nodes distant.

In this system a given node is responsible for sensing the response signal from one or more receiving coils. The node may use an amplifier to increase the level of the signal and may contain a suitable filter for removing noise from the received signal. These functions are distributed amongst components such that a parallel signal path, using the same components may be used to measure a reference signal. In this way, long term drift can be controlled. Alternately, a given node may use a suitably high-resolution analog-to-digital, (A/D) converter, or ADC, to recover the response signal. In this case, filtering may be done by using standard digital filtering techniques.

With regard to FIG. 2, the electronic system is composed of two major functional blocks: The "Base Board" and the "Application Board". The Base Board accepts external power and includes a power regulation module 100 that to meet its needs. The Base Board holds a (usually low power) microprocessor 103, some local memory 104, a serial port 102 and a wireless communications link 101. These resources are common to all applications. The Base Board provides a set of resources for use by the Application Board, including an application board control/acquisition interface 105. A typical set of services include digital I/O, internal ADC, internal DAC, PWM, timers, and an SPI bus.

The Application Board is tailored to a specific need; in this case, the hardware required for the Corrosion Detection System. This system includes a plurality of PWM drivers 106 which connect to externally mounted Drive Coils 107. There are four such pairs shown in FIG. 2; however, the actual number may be larger or smaller. There are also Receiving or Response Coils 108 that are externally mounted, which are sampled by a high-resolution ADC 109. Again, four sets of response coils have been shown; however, the actual number may be larger or smaller. Finally, the Application Board has provisions for local power regulation 111. A buffer 110 is provided to connect off-board sensors such as temperature, pressure, and strain sensors 150-152 described previously to the application board and thus the base board of the system.

There are two pertinent perspectives in regards to data acquisition. One can view the system from an external perspective, the view from the "Host System". Alternatively, one can focus on the internal perspective, the view from the "Node Processor". The Host System interacts with a Node to run a trial. As shown in FIG. 3, the method for running a trial begins at step 200 where one block of data is sent to the target node for each active driver used in this trial. This block includes the ID of the driver, the type of waveform it will generate, the amplitude of the output signal, the relative offset of the output signal and the relative phase of the output signal. In step 201 a single block of data is sent to the target node that holds the overall trial parameters. This block includes an ID for the current trial, the frequency of the signal to generate, the number of samples taken per cycle, the number of cycles to "hold-off" (i.e., the number of cycles to run before sampling starts), the number of cycles over which sampling will occur, a mask of receiver coils that will be used in the trial and a mask of drivers that will be used for the trial. Thus, the total number of cycles specified is equal to the number of "hold-off" cycles plus the number of cycles of active sampling. The order in which the driver data [200] and the trial data [201] is sent is unimportant.

Once all of the trial parameters have been set (in steps 200 and 201) the trial is initiated. The Host System now sets a timer and waits (step 202) for the trial to complete. On expiration of the timer, the Host System requests in step 203 that the node send back the data taken for a particular drive. This process is repeated for each active drive used in the trial. In step 204 the Host System requests the node to send back the data taken from a particular response coil. This process is repeated for each active response coil. The order in which Drive Data 202 and Response Data 203 steps are taken is of no importance. Finally, in step 205 the Host System requests the node to send back the contents of its status array.

From the Node Processor perspective, a trial begins after all parameters have been passed to the node. Referring back to FIG. 3, this means that Driver Parameters 200 and the Trial Parameters 201 steps have been carried out and that the Host System is waiting for the trial to complete [202]. With reference to FIG. 4, the Node Processor begins a trial during the wait state of step 202 by building an array of output values for each active drive, as shown in step 300. The data points are calculated from the parameters sent by the Host System in steps 200 and 201. Once the driver arrays have been built, in step 301 the Node Processor allocates the necessary internal resources to run the trial. This includes (but is not limited to) setting timers and initializing counters. The externally visible start of the trial commences in step 302 with the output of the requested number of "Hold-Off" cycles. A hold-off cycle generates current in the drive coils. However, no data is sampled during this time.

After the required number of hold-off cycles have been run, the Node Processor begins acquiring data in step 303. Samples are taken from each of the active Drivers in order to verify and quantify the amount of drive signal used. Samples are taken from each of the active Response Coil sensors. This data is stored in local memory for later retrieval.

When the required number of samples has been acquired, the Node Processor in step 304 turns off the drive signals and release all previously allocated resources. Once a trial run has finished, the data is stored as a measurement of the difference between the drive signal level and the response signal level. This data provides a measure proportional to the number of magnetic domains carrying energy from the driver coil to the receiver coil. By making trial runs over significant intervals of time, any and all deterioration in the ferromagnetic pipe will be recorded as a change of the level of the response signal in the receiver coil(s) relative to the drive signal(s). This is an accurate measurement of corrosion or other deterioration of the pipe. This data may be combined with the data from sensors 150-152 to record changes in pipe integrity as well as ambient operating conditions. This data may be used to predict ongoing maintenance or replacement of the pipe, or to issue alarm warnings if sudden changes occur in the pipe or its ambient conditions.

Figure 6:
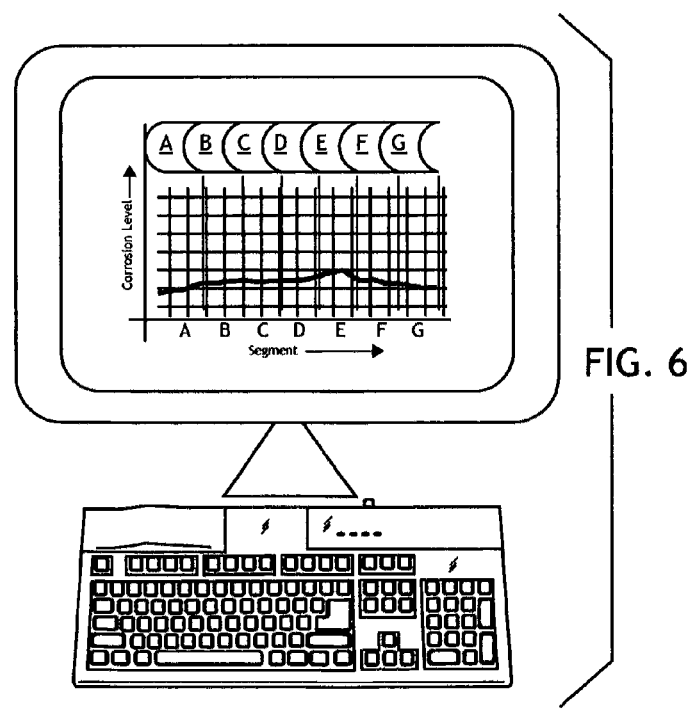
FIG. 6 depicts a graphic illustration of the data obtained by the magnetic response imaging system.

With reference to FIG. 6, the data generated by the system described above may be portrayed on a computer display, with the pipeline monitored segments A-G pictured extending laterally at the upper portion and a plot of the corrosion level versus monitored segment rendered therebelow in direct alignment therewith. Thus the system provides an image of the corrosion in the pipeline sidewall. The system may also display a plot of changes in corrosion level over time at each monitored segment, or other such graphic outputs.

It is noted that the invention is described with reference to ferromagnetic pipes and vessels. However, the invention may be extended to virtually any object that has ferromagnetic properties and is subject to corrosion and/or deterioration. For example, structural steel members in bridges, buildings, foundations, dams and the like may be monitored by the present invention. In addition, vessels such as nuclear containment vessels, which may be caused to deteriorate due to high radiation exposure, may also be monitored by the invention, particularly since the monitoring system is maintained on the exterior surface of the vessel and has no internal vessel exposure.

The foregoing description of the preferred embodiments of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

The invention claimed is:

1. A method for monitoring corrosion and deterioration of a ferromagnetic vessel having a vessel wall, including the steps of:
    providing a plurality of drive coils and securing said drive coils to the exterior surface of said vessel wall, said drive coils being spaced apart on said vessel wall;
    providing a plurality of response coils and securing said response coils to the exterior surface of said vessel wall, said response coils being spaced apart on said vessel wall;
    transmitting a drive current through at least one of said drive coils to create a magnetic signal that propagates through the magnetic domains of said vessel wall;
    at least one of said response coils receiving said magnetic signal which in turn generates a response signal in said response coil;
    quantifying said drive current and said response signal and recording said drive current and response signal; and,
    comparing said drive current and response signal to previous data and threshold levels to determine corrosion and deterioration in said vessel wall.

2. The method of claim 1, wherein each of said drive coils is paired with a respective one of said response coils in adjacent, closely spaced relationship to form a coil pair.

3. The method of claim 2, wherein each coil pair substantially circumscribes said vessel.

4. The method of claim 2, wherein each coil of said coil pair is wound in a nominal plane, said nominal plane then being curved to conform to an outer surface curvature of said vessel wall.

5. The method of claim 1, wherein said drive current comprises an AC signal selected from one of the group including AC sine wave, AC square wave, digital signal, and PWM signal.

6. The method of claim 5, further including the step of providing a plurality of driver modules, each adapted to deliver said drive current to one of said drive coils.

7. The method of claim 6, further including the step of providing a high resolution ADC connected to receive said response signals from said response coils, and microprocessor means for addressing said driver modules and said ADC for selecting at least one specific drive coil to receive said drive current and at least one specific response coil having its response signals processed through said ADC and transmitted to said microprocessor means.

8. The method of claim 7, wherein said at least one specific drive coil and said at least one specific response coil comprises a node that is processed by said microprocessor means.

9. The method of claim 8, further including the step of processing a plurality of nodes in serial fashion, each of said plurality of nodes comprising a unique combination of said at least one drive coil and said at least one response coil.

10. The method of claim 9, wherein each of said drive coils is paired with a respective one of said response coils in adjacent, closely spaced relationship to form a coil pair, and each of said nodes includes at least one of said coil pairs.

11. The method of claim 1, further including the step of providing at least one sensor for detecting an ambient condition of said vessel, said at least one sensor being selected from a group consisting of one or more of the following: temperature sensor, strain sensor, and pressure sensor.

12. The method of claim 11, including the step of providing microprocessor means for recording the outputs of said at least one sensor contemporaneously in association with recording said drive current and said response signal.

13. The method of claim 9, further including the step of reiterating said processing of said nodes over a long time period to collect a history of data indicating changes in the magnetic domains of said vessel.

14. The method of claim 12, further including the step of modifying said data on said drive current and said response signal in accordance with said outputs of said at least one sensor.

15. The method of claim 1, further including the step of digitizing and stabilizing said drive current to maintain the same drive current during test runs reiterated over long periods of time.

16. The method of claim 11, further including the step of digitizing and correcting said response signal in correspondence with the output of said at least one sensor, whereby said response signal is corrected for fluctuations in said ambient condition.

17. The method of 16, wherein said at least one sensor comprises a temperature sensor.

18. The method of claim 1, further including the step of using one or more of said response coils for determining noise and fluctuation levels for use in providing stable determinations of the status of corrosion and other deterioration in said vessel wall.

19. A system for monitoring corrosion and deterioration of a ferromagnetic object, including:
- a plurality of drive coils and means for securing said drive coils to the exterior surface of said object, said drive coils being spaced apart on said object
- a plurality of response coils and means for securing said response coils to the exterior surface of said object, said response coils being spaced apart on said object;
- means for transmitting a drive current through at least one of said drive coils to create a magnetic signal that propagates through the magnetic domains of said object;
- at least one of said response coils receiving said magnetic signal which in turn generates a response signal in said response coil;
- means for quantifying said drive current and said response signal and recording said drive current and response signal; and,
- means for comparing said drive current and response signal to previous data and threshold levels to determine corrosion and deterioration in said vessel wall.

20. The system of claim 19, further including means for displaying said corrosion and deterioration in said vessel wall versus position along said vessel wall.

21. The system of claim 19, further including a non-ferromagnetic insulating material interposed between said exterior surface and said drive coils and response coils, said magnetic signal penetrating said insulating material and propagating through said magnetic domains of said object.

* * * * *